(12) United States Patent
Seelig et al.

(10) Patent No.: US 7,189,243 B1
(45) Date of Patent: Mar. 13, 2007

(54) ORTHOPAEDIC FIXATION PIN EXTRACTION

(75) Inventors: Matthew Seelig, Upper Saddle River, NJ (US); Jack O'Loughlin, Limerick (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 205 days.

(21) Appl. No.: 10/813,914

(22) Filed: Mar. 31, 2004

(51) Int. Cl.
*A61B 17/88* (2006.01)

(52) U.S. Cl. ..................................... 606/104

(58) Field of Classification Search ................. 606/99, 606/103, 104; 81/9.41–9.43, 126, 362; 254/18–24
See application file for complete search history.

(56) References Cited

U.S. PATENT DOCUMENTS

| | | | |
|---|---|---|---|
| 1,188,931 A | 6/1916 | Gray | |
| 1,623,912 A | 4/1927 | Dunn et al. | |
| 1,730,980 A * | 10/1929 | Montgomery | 81/9.42 |
| 3,143,903 A * | 8/1964 | Van Hecke | 29/243.522 |
| 3,164,283 A * | 1/1965 | Olson | 29/243.523 |
| 3,422,708 A * | 1/1969 | Bieganski | 81/9.43 |
| 3,886,782 A * | 6/1975 | Miyamoto | 29/243.528 |
| 4,028,790 A * | 6/1977 | Dupuis | 29/764 |
| 4,285,123 A * | 8/1981 | Chisholm | 29/764 |
| 4,311,069 A | 1/1982 | Walker | |
| 4,625,538 A | 12/1986 | Malagnoux | |
| 4,627,420 A | 12/1986 | Katz | |
| 4,765,206 A | 8/1988 | Poehlmann | |
| 4,817,274 A | 4/1989 | Higgins | |
| 4,932,638 A | 6/1990 | Chen | |
| 5,566,924 A | 10/1996 | Shirk | |
| 6,042,585 A * | 3/2000 | Norman | 606/104 |
| 6,066,143 A | 5/2000 | Lane | |
| 6,364,288 B1 * | 4/2002 | Laughlin | 254/18 |
| 6,481,691 B1 * | 11/2002 | Irving | 254/28 |

* cited by examiner

*Primary Examiner*—Eduardo C. Robert
*Assistant Examiner*—Richard Shaffer
(74) *Attorney, Agent, or Firm*—Arthur Jacob

(57) ABSTRACT

An instrument and a method for gripping an orthopaedic fixation pin during a surgical procedure and extracting the pin from bone in which the pin is embedded. The pin has an embedded portion extending into the bone along a longitudinal axis, and a projecting portion projecting longitudinally from the bone adjacent a bearing surface associated with the bone. The instrument and the method enable gripping of the projecting portion of the pin between gripping elements which are moved laterally relative to one another to grip the projecting portion of the pin and then are moved longitudinally by urging a plunger against the bearing surface to pull the pin along a linear path essentially parallel to the longitudinal axis so as to withdraw the embedded portion of the pin from the bone along a direction parallel to the longitudinal axis.

9 Claims, 5 Drawing Sheets

ORTHOPAEDIC FIXATION PIN EXTRACTION

The present invention relates generally to the facilitation of surgical procedures which employ orthopaedic fixation pins embedded in bone and pertains, more specifically, to the withdrawal and extraction of such pins from the bone upon completion of a surgical procedure which utilizes these pins.

It is quite common in surgical procedures involving the repair of bone or the implant of prosthetic devices, such as prosthetic joints, to utilize fixation pins for locating and temporarily securing in place various guides and instruments usually employed in the preparation of bone for the reception of these devices. Once the fixation pins have served their purpose, they are removed from the bone. It is important that extraction of the fixation pins be accomplished with minimal effort and with adequate control, while avoiding damage to the bone in the vicinity of the site.

Instruments have been proposed for pulling fixation pins from bone. One such instrument is disclosed in U.S. Pat. No. 6,066,143, wherein a hand-operated device engages the head of a headed fixation pin, or an undercut in the pin, to impart an axial force to the pin and pull the pin smoothly out of the bone along a linear path which avoids damage to the surrounding bone. However, many fixation pins currently in use do not include a lateral surface, such as a head or an undercut, and are not amenable to withdrawal using an instrument which requires engagement with a lateral surface on the pin. Moreover, reliance upon engagement of a head or an undercut on the pin requires an instrument capable of operating over a pulling stroke long enough to accommodate the removal of longer as well as shorter pins without the need for an excessively long instrument or one requiring complex adjustments or modification.

The present invention facilitates withdrawal and extraction of a fixation pin from bone without relying upon engaging a lateral surface on the pin. As such, the present invention attains several objects and advantages, some of which are summarized as follows: Provides an instrument and a method by which a longitudinally projecting portion of a fixation pin embedded in bone is gripped and moved to withdraw the pin from the bone along a linear path which avoids damage to surrounding bone; facilitates the extraction of a fixation pin embedded in bone with an instrument readily operated by one hand; enables effective removal of a wider variety of fixation pins, including fixation pins having no lateral surfaces which can be engaged for exerting longitudinal pulling forces upon the pins, and fixation pins of different lengths and varying degrees of extension into bone; employs a simple and effective mechanism, readily operated with one hand, for gripping an embedded fixation pin and exerting sufficient force directed along the pin to enable a fully-controlled, ready withdrawal of the pin while avoiding damage to surrounding bone; enables the gripping of a fixation pin at essentially-any location along the length of the pin without requiring a particular pin configuration at a gripped location, and with a gripping force in keeping with applying a pulling force sufficient to extract the pin from the bone; provides a surgical instrument constructed for ease of cleaning and sterilization for long-term service in surgical procedures; incorporates an ergonomically effective design and simplified procedure for use in facilitating fully-controlled extraction of fixation pins from bone; provides a rugged construction for reliable operation over and extended service life.

The above objects and advantages, as well as further objects and advantages, are attained by the present invention which may be described briefly as an instrument for gripping an orthopaedic fixation pin during a surgical procedure and extracting the pin from bone in which the pin is embedded, the pin having an embedded portion extending into the bone along a longitudinal axis, and a projecting portion projecting longitudinally from the bone adjacent a bearing surface associated with the bone, the instrument comprising: a first handle member; a second handle member coupled with the first handle member for selective movement relative to the first handle member between a first position and a second position; a pusher coupled with the first and second handle members for movement relative to the first and second handle members in directions along a linear path essentially parallel to the longitudinal axis in response to movement of the second handle member between the first and second positions; and a gripping mechanism including first and second gripping elements coupled with the first and second handle members for movement to grip the projecting portion of the pin between the first gripping element and the second gripping element in response to an initial movement of the second handle member from the first position toward a second position; the second handle member being coupled to the pusher such that upon movement of the second handle member relative to the first handle member farther toward the second position, subsequent to the initial movement, the pusher is urged against the bearing surface to move the gripping mechanism away from the bearing surface and to establish an extraction force in a direction essentially parallel to the longitudinal axis, and the gripped projecting portion of the pin is moved with the gripping mechanism to withdraw the embedded portion of the pin from the bone along a direction essentially parallel to the longitudinal axis.

In addition, the present invention provides A method for gripping an orthopaedic fixation pin during a surgical procedure and extracting the pin from bone in which the pin is embedded, the pin having an embedded portion extending into the bone along a longitudinal axis, and a projecting portion projecting longitudinally from the bone adjacent a bearing surface associated with the bone, the method comprising: gripping the pin along the longitudinally projecting portion by gripping the longitudinally projecting portion between first and second gripping elements movable laterally relative to one another to grip the longitudinally projecting portion of the pin within a gripping mechanism with a gripping force; and urging a plunger against the bearing surface in a direction parallel to the longitudinal axis to move the gripping mechanism along a longitudinal direction of movement parallel to the longitudinal axis, away from the bearing surface, to pull the embedded portion of the pin from the bone with a withdrawal force.

The invention will be understood more fully, while still further objects and advantages will become apparent, in the following detailed description of preferred embodiments of the invention illustrated in the accompanying drawing, in which.

Figure 1:
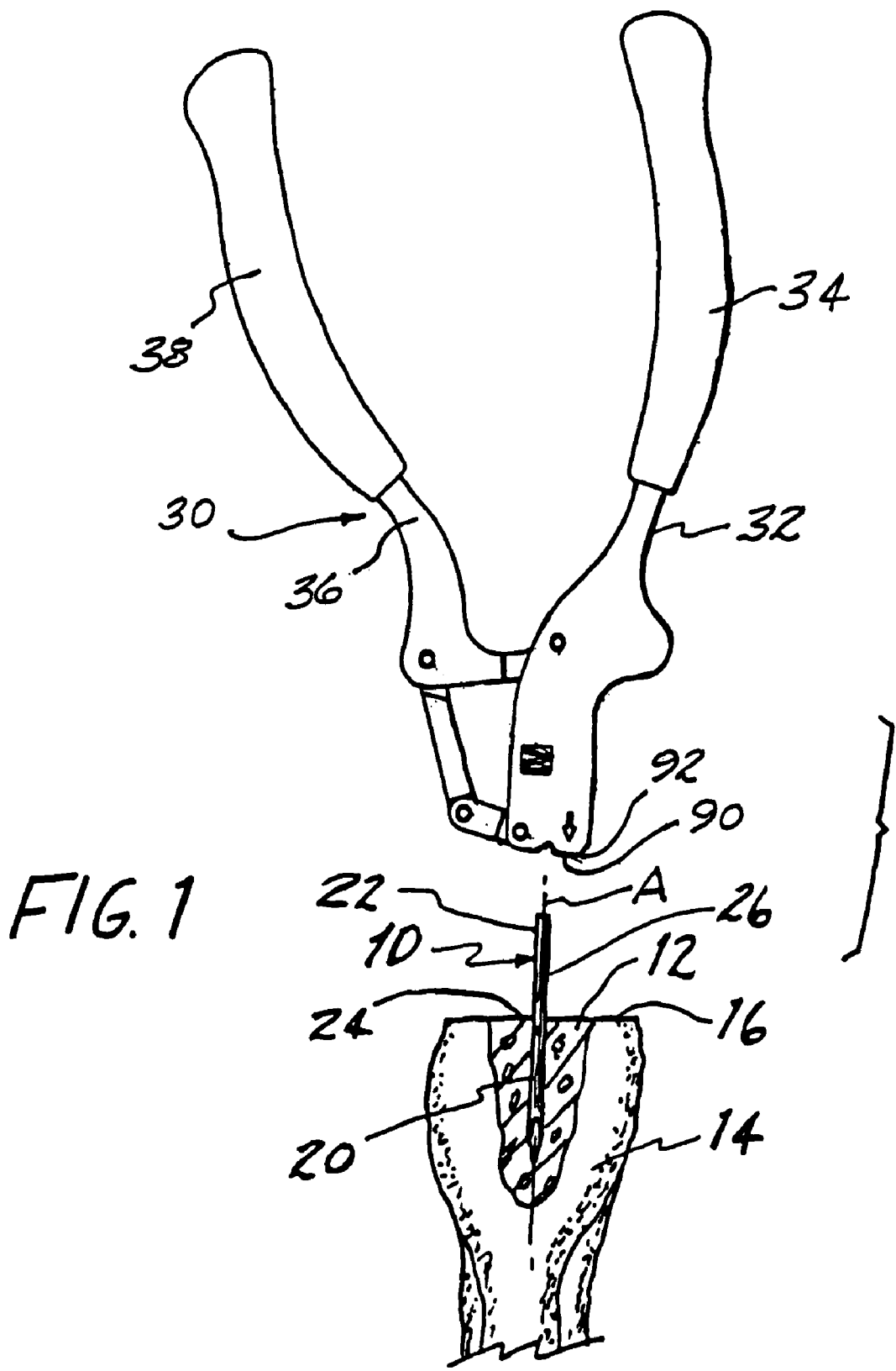
FIG. 1 is a pictorial and largely elevational view showing an instrument constructed in accordance with the present invention and being utilized in a method of the invention.

Referring now to the drawing, and especially to FIG. 1 thereof, an orthopaedic fixation pin 10 is shown embedded in bone 12, illustrated in the form of a proximal tibia 14 having a face 16 prepared for the reception of a tibial component of a knee prosthesis (not shown). Fixation pin 10 has a generally cylindrical configuration and includes an embedded portion 20 extending into bone 12 along a longitudinal axis shown in the form of a central axis A, and a projecting portion 22 projecting longitudinally from face 16 adjacent a bearing surface 24 extending along face 16. The cylindrical configuration of pin 10 provides a smooth cylindrical external surface 26 extending along the length of the pin 10, uninterrupted by any head, undercut or other lateral surface which could impede the use of pin 10 for locating a cutting guide or the like at the proximal tibia 14 during preparation of the proximal tibia 14 for the reception of a tibial implant component.

Upon completion of the preparation of proximal tibia 14, fixation pin 10 is to be extracted from bone 12. Pin 10 is secured within bone 12 by a frictional engagement, akin to the anchoring of a nail within a substrate, and requires force to withdraw the pin 10 from the bone 12. In order to avoid damage to bone 12, particularly in the vicinity of bearing surface 24, any pulling, or extraction force exerted on pin 10 should best be directed along a linear path coextensive with axis A so that pin 10 is pulled from bone 12 in a direction essentially parallel with axis A. At the same time, the pulling, or extraction force should be fully-controlled so as to preclude any sudden release of pin 10 and consequent uncontrolled movements of the pin 10 and any instrument used to pull the pin 10 from the bone 12.

An instrument constructed in accordance with the present invention is shown at 30 and is seen to include a first handle member 32 having a first handgrip 34 and a second handle member 36 having a second handgrip 38. In a one-handed manipulation, instrument 30 is to be slipped over projecting portion 22 of pin 10, and then operated to grip projecting portion 22 and withdraw pin 10 from bone 12 by moving handle members 32 and 36 toward one another, all in a manner fully described below.

Figure 2:
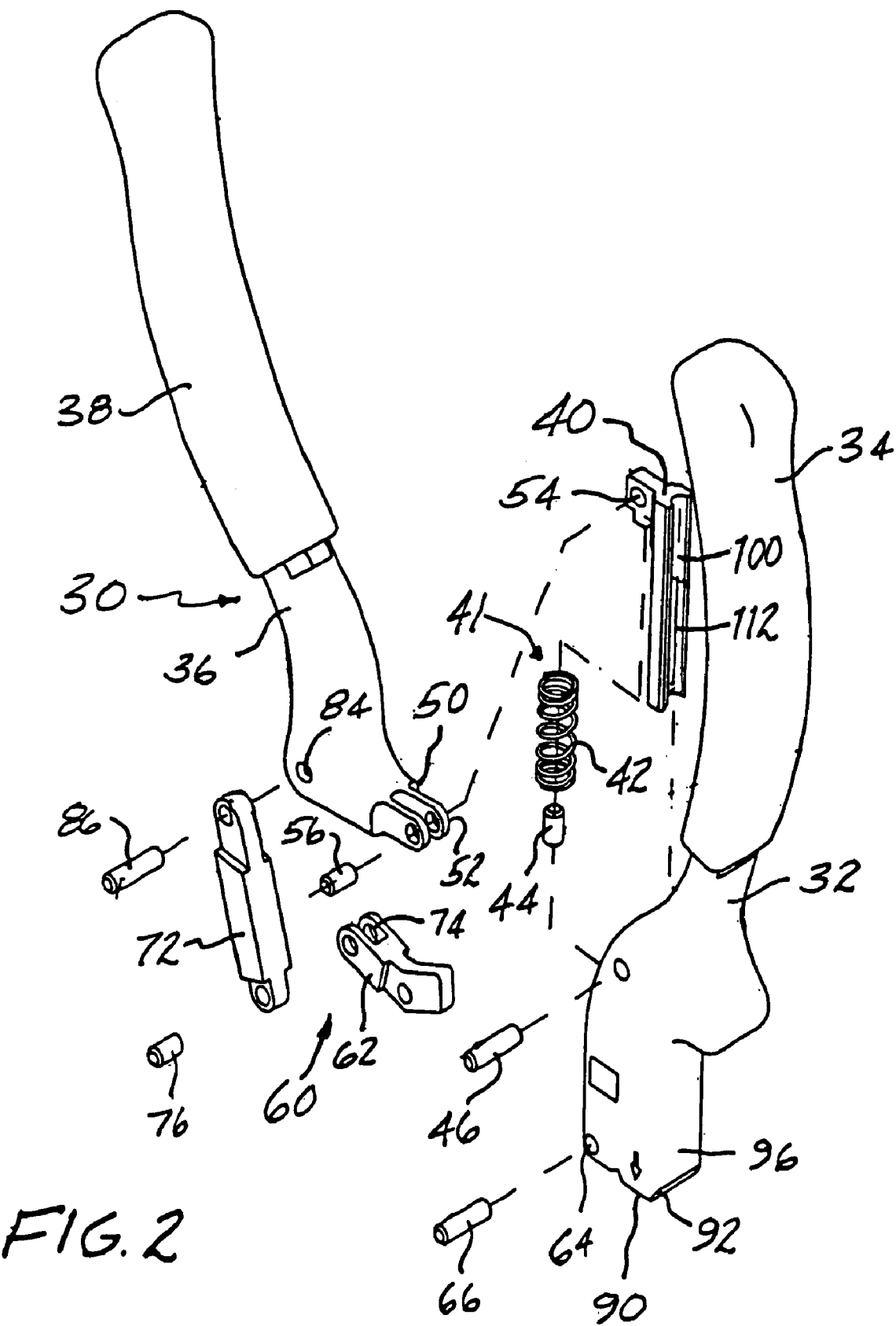
FIG. 2 is an exploded perspective view of the instrument.

As illustrated in FIG. 2, instrument 30 includes several component parts. In addition to first and second handle members 32 and 36, instrument 30 includes a pusher in the form of a plunger 40 arranged for sliding movement within the first handle member 32, and a biasing mechanism 41 which includes a helical spring 42 extending between a post 44 and the plunger 40 for biasing the plunger 40 toward a retracted position within the first handle member 32, wherein the plunger 40 engages a stop pin 46, as will be made apparent below. The second handle member 36 includes an arm 50 which extends laterally and carries a clevis 52 to be coupled with the plunger 40 at 54 by a clevis pin 56.

A linkage system 60 couples the second handle member 36 with the first handle member 32 and includes a first link 62 pivotally connected to the first handle member 32 at 64 by a pivot pin 66. A second link 72 is pivotally connected to first link 62 at 74 by a pivot pin 76 and is pivotally connected to second handle member 36 at 84 by a pivot pin 86.

Figure 3:
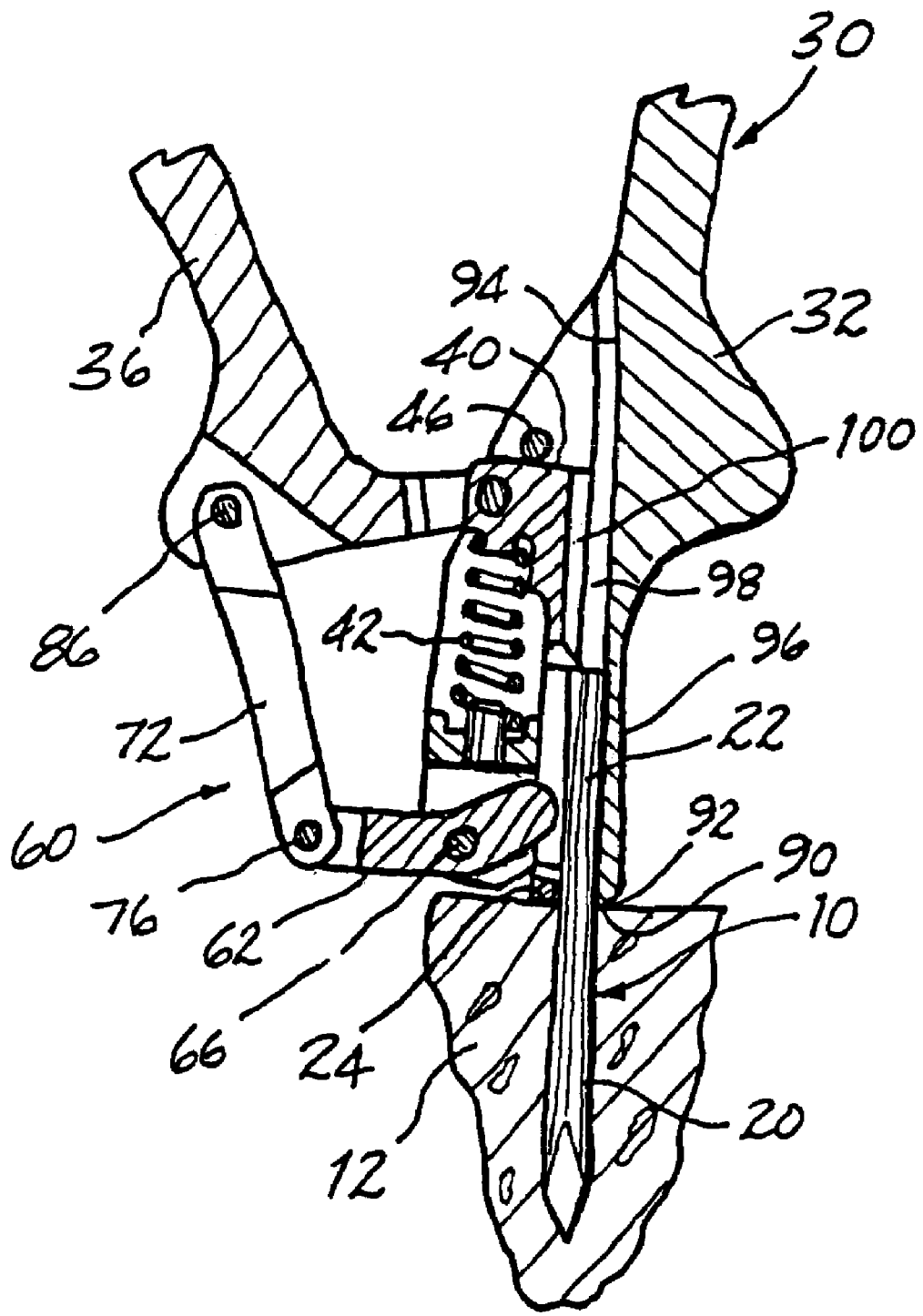
FIG. 3 is a somewhat diagrammatic, enlarged fragmentary longitudinal cross-sectional view of the instrument being utilized in the method.

Referring now to FIG. 3, instrument 30 has been slipped over projecting portion 22 of pin 10 such that first handle member 32 rests upon the bone 12 adjacent bearing surface 24 of bone 12, along a basal surface 90 located at a basal end 92 of the first handle member 32. The projecting portion 22 is received within a channel 94 which runs longitudinally along the instrument 30 such that the projecting portion 22 is seated between a depending neck portion 96 of the first handle member 32 and the plunger 40. Plunger 40 is mounted for sliding movement in longitudinal directions within the first handle member 32 and is shown biased by spring 42 into the retracted position against stop pin 46. Channel 94 includes a surface 98 extending along neck portion 96 and having a partially cylindrical surface contour configuration generally complementary to the external surface contour configuration of projecting portion 22 of pin 10, and plunger 40 includes a longitudinal groove 100 which also has a partially cylindrical surface contour configuration generally complementary to the external surface contour configuration of projecting portion 22 of pin 10 so that projecting portion 22 is received and closely confined between neck portion 96 and plunger 40.

Figure 4:
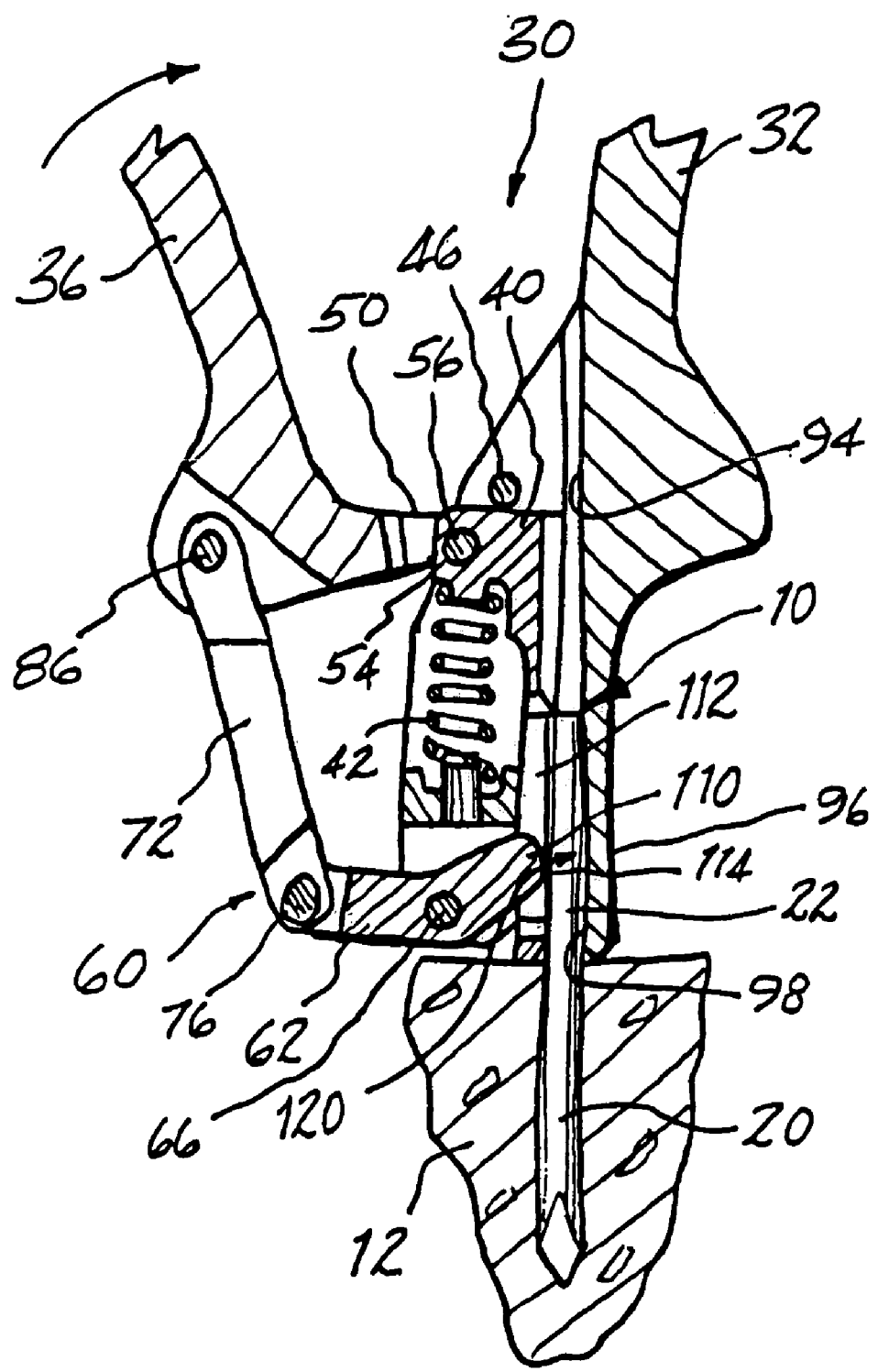
FIG. 4 is a view similar to FIG. 3 and showing the instrument and method in another stage of use.

Turning now to FIG. 4, as second handle member 36 is moved toward first handle member 32, initial movement of second handle member 36 from the first position shown in FIG. 3 to an intermediate position shown in FIG. 4 rotates the second handle member 36 in a clockwise direction about clevis pin 56, as viewed in FIG. 4, and draws link 72 generally upwardly to rotate link 62 in a clockwise direction, thereby moving a gripping finger 110, carried by link 62 and extending through a slot 112 in plunger 40, laterally into engagement with the projecting portion 22 of pin 10 at 114. During this initial movement, plunger 40 and clevis pin 56 remain essentially stationary, by virtue of a predetermined biasing force exerted by spring 42 to retain plunger 40 at the retracted position, and the increased force applied to move second handle 36 toward first handle 32 is transmitted through linkage system 60 so that link 62 and neck portion 96 serve as a gripping mechanism 120 in which the surface 98 of the channel 94 of neck portion 96 acts as a gripping surface on a first gripping element, and the finger 110 of link 62 acts as a second gripping element to grip the projecting portion 22 of pin 10 between the neck portion 96 and the link 62, with a gripping force sufficient to secure the pin 10 against any relative movement between the pin 10 and the neck portion 96 of the instrument 30.

Figure 5:
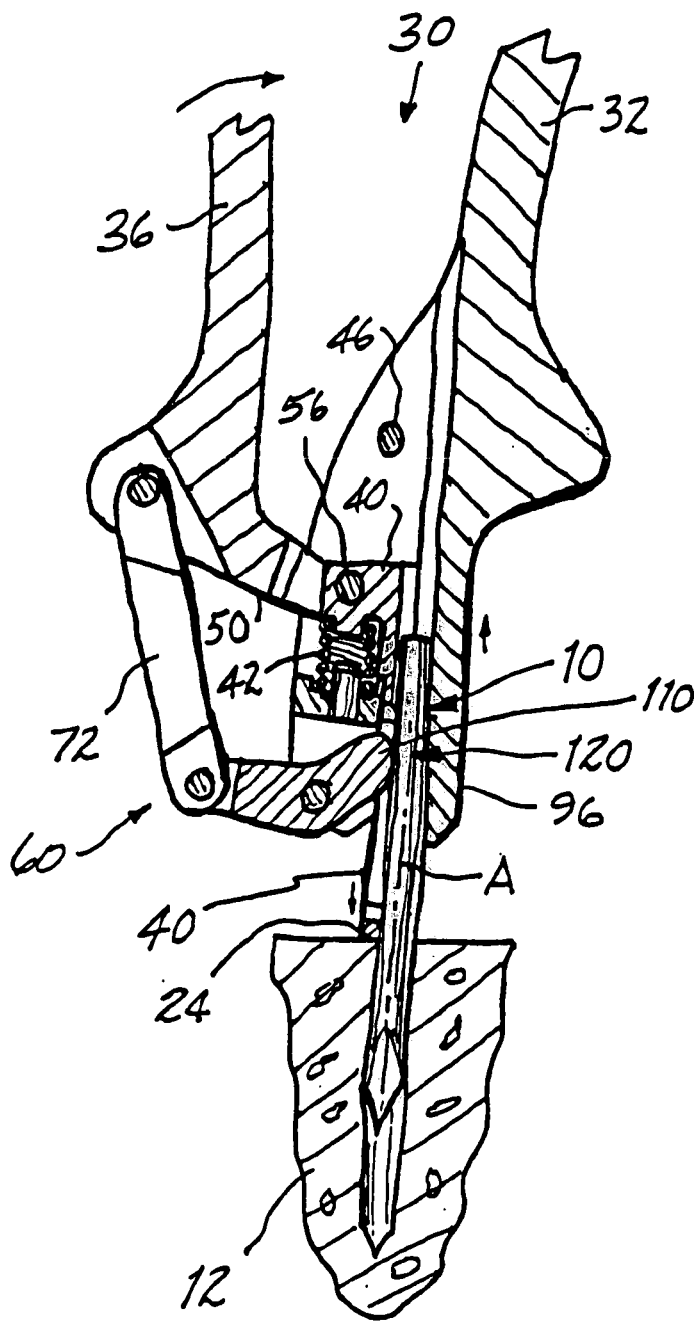
FIG. 5 is a view similar to FIG. 3 and showing the instrument and method in still another stage of use.

Upon continued movement of the second handle member 36 toward the first handle member 32, subsequent to the above-described initial movement, pivotal movement of the second handle member 36 about pivot pin 86 moves arm 50 in a clockwise direction, as seen in FIG. 5, and arm 50 serves as an actuator urging plunger 40 downwardly, away from the retracted position, against the biasing force of spring 42, by virtue of the coupling of arm 50 with the plunger 40 at 54. Movement of the plunger 40 downwardly, away from the retracted position, advances the plunger 40 toward the advanced position illustrated in FIG. 5 and urges the plunger 40 against the bearing surface 24 of bone 12 with a force which establishes a pulling force sufficient to raise the first handle member 32, together with gripping mechanism 120, and thereby withdraw pin 10 from bone 12.

The force exerted by plunger 40 upon bearing surface 24 of bone 12 is placed closely adjacent pin 10 and is in a direction extending along pin 10, essentially parallel to axis A, so that the pulling force pulls pin 10 from bone 12 along a linear path in a direction which avoids damage to bone 12, as well as any damage to pin 10. At the same time, pin 10 is withdrawn smoothly and with ease, by virtue of the ease of control of the movement of second handle 36 toward first handle 32, so as to enable a fully-controlled extraction force, avoiding any abrupt movements of pin 10 or instrument 30 which could engender deleterious results during a surgical procedure. Further, the arrangement of the first and second handle members 32 and 36, in combination with the linkage system 60 and biasing mechanism 41, allows a simplified, single-hand operation to initially grip and subsequently exert a controlled pulling force on pin 10 to extract pin 10 from bone 12 with ease and precision.

The configuration of linkage system 60 operating in concert with biasing mechanism 41 assures that a sufficient gripping force is established prior to exerting a pulling force on pin 10. In addition, the configuration of linkage system 60 is such that the gripping force with which the gripping mechanism 120 grips pin 10 is varied in direct proportion to the pulling force needed to extract pin 10 from bone 12, that is, the gripping force is in keeping with the pulling force so that the force required to operate instrument 30 is held to a minimum consistent with a controlled, single-handed operation in which pin 10 is extracted from bone 12. Moreover, the ability of gripping mechanism 120 to grip pin 10 at virtually any location along pin 10, without requiring a head, an undercut or any other laterally extending surfaces at fixed locations along the length of a pin, allows instrument 30 effectively to fully withdraw pins 10 of different lengths and of varying degrees of extension into bone 12 without modification of the instrument 30, the complete extraction of longer pins having a greater extension into bone merely requiring repeat, sequential operations of instrument 30 for concomitant sequential increments of withdrawal until the pin is pulled entirely free of the bone.

Figure 6:
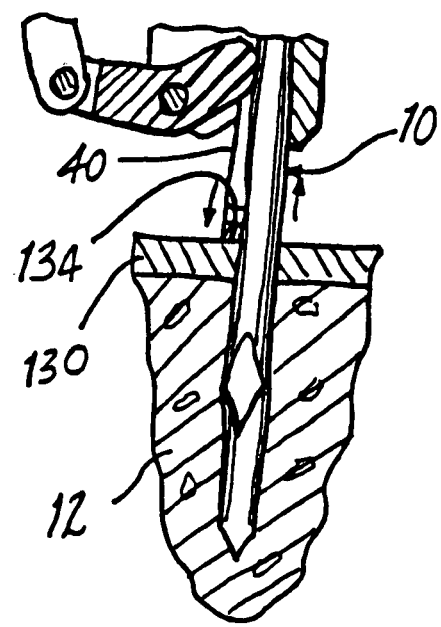
FIG. 6 is a fragmentary view similar to FIG. 5 and showing an alternate utilization of the instrument.

Alternately, pin 10 can be extracted while an instrument, such as a cutting guide, remains in place on the bone. Thus, as seen in FIG. 6, a cutting guide 130 is in place on bone 12 and plunger 40 is urged against a bearing surface 134 on the cutting guide 130 to extract pin 10 from bone 12. In either event, the location of plunger 40 immediately adjacent pin 10 assures an appropriately directed pulling force for smooth extraction of pin 10.

It will be apparent that the present invention attains all of the objects and advantages summarized above, namely: Provides an instrument and a method by which a longitudinally projecting portion of a fixation pin embedded in bone is gripped and moved to withdraw the pin from the bone along a linear path which avoids damage to surrounding bone; facilitates the extraction of a fixation pin embedded in bone with an instrument readily operated by one hand; enables effective removal of a wider variety of fixation pins, including fixation pins having no lateral surfaces which can be engaged for exerting longitudinal pulling forces upon the pins, and fixation pins of different lengths and varying degrees of extension into bone; employs a simple and effective mechanism, readily operated with one hand, for gripping an embedded fixation pin and exerting sufficient force directed along the pin to enable a fully-controlled, ready withdrawal of the pin while avoiding damage to surrounding bone; enables the gripping of a fixation pin at essentially an location along the length of the pin without requiring a particular pin configuration at a gripped location, and with a gripping force in keeping with applying a pulling force sufficient to extract the pin from the bone; provides a surgical instrument constructed for ease of cleaning and sterilization for long-term service in surgical procedures; incorporates an ergonomically effective design and simplified procedure for use in facilitating fully-controlled extraction of fixation pins from bone; provides a rugged construction for reliable operation over and extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An instrument for gripping an orthopaedic fixation pin during a surgical procedure and extracting the pin from bone in which the pin is embedded, the pin having an embedded portion extending into the bone along a longitudinal axis, and a projecting portion projecting longitudinally from the bone adjacent a bearing surface associated with the bone, the instrument comprising:
   a first handle member having a first gripping element including a gripping surface;
   a second handle member coupled with the first handle member for selective movement relative to the first handle member between a first position and a second position;
   a pusher coupled with the first and second handle members for movement relative to the first and second handle members in directions along a linear path essentially parallel to the longitudinal axis in response to movement of the second handle member between the first and second positions;
   a gripping mechanism including the first gripping element and a second gripping element coupled with the first and second handle members for movement to grip the projecting portion of the pin between the first gripping element and the second gripping element in response to an initial movement of the second handle member from the first position toward the second position;
   the second gripping element including a gripping finger mounted upon the first handle member for movement toward and away from the gripping surface; and
   a linkage system coupling the second handle member with the gripping finger for movement of the gripping finger laterally toward the gripping surface in response to movement of the second handle member from the first position toward the second position;
   the second handle member being coupled to the pusher such that upon movement of the second handle member relative to the first handle member farther toward the second position, subsequent to the initial movement, the pusher is urged against the bearing surface to move the gripping mechanism away from the bearing surface and to establish an extraction force in a direction essentially parallel to the longitudinal axis, and the gripped projecting portion of the pin is moved with the gripping mechanism to withdraw the embedded portion of the pin from the bone along a direction essentially parallel to the longitudinal axis.

2. The instrument of claim 1 wherein the pusher comprises a plunger mounted upon the first handle member for sliding movement in directions essentially parallel to the longitudinal direction.

3. The instrument of claim 2 wherein the gripping surface includes a first contour configuration, and the plunger has a second contour configuration, the first and second contour configurations being dimensioned and configured for essentially confining the pin closely between the gripping surface and the plunger.

4. The instrument of claim 3 wherein the first and second contour configurations each comprise a partially cylindrical contour configuration.

5. The instrument of claim 2 wherein the plunger is mounted for movement between a retracted position, wherein the plunger is retracted toward the first handle member, and an advanced position, wherein the plunger is advanced from the first handle member against the bearing surface, the instrument including:

a biasing mechanism for biasing the plunger toward the retracted position with a predetermined biasing force; and an actuator carried by the second handle member for urging the plunger toward the advanced position, against the predetermined biasing force of the biasing mechanism, in response to movement of the second handle member from the first position toward the second position.

6. The instrument of claim 5 wherein the linkage system is configured for urging the gripping finger toward the gripping surface to establish a gripping force, in response the initial movement of the second handle member toward the first handle member, and for urging the plunger toward the advanced position to establish an extraction force in response to movement of the second handle member beyond the initial movement toward the second position, with the gripping force established prior to establishment of the extraction force, by virtue of the predetermined biasing force.

7. The instrument of claim 6 wherein the actuator includes an arm on the second handle member, the arm being coupled with the biasing mechanism such that the biasing mechanism biases the second handle member toward the first position.

8. The instrument of claim 7 wherein the biasing member includes a spring positioned and configured for biasing the plunger toward the retracted position and the second handle member toward the first position.

9. The instrument of claim 1 wherein the second handle member is mounted for pivotal movement relative to the first handle member.

* * * * *